United States Patent [19]

Berkoz et al.

[11] 4,064,257

[45] Dec. 20, 1977

[54] THIAZOLE CARDIOVASCULAR AGENTS

[75] Inventors: Belig M. Berkoz, Los Altos; Brian Lewis, Mountain View; Stefan H. Unger, Palo Alto, all of Calif.

[73] Assignee: Syntex (U.S.A.) Inc., Palo Alto, Calif.

[21] Appl. No.: 706,341

[22] Filed: July 19, 1976

[51] Int. Cl.$^2$ .................. C07D 277/56; A61K 31/425
[52] U.S. Cl. ............................. 424/270; 260/295.5 S; 260/302 H; 260/302 R; 424/266
[58] Field of Search ............................... 424/270, 266; 260/302 R, 302 H, 295.5 S

[56] References Cited

U.S. PATENT DOCUMENTS

| | | | |
|---|---|---|---|
| 3,850,946 | 11/1974 | Edwards | 260/302 R |
| 3,850,947 | 11/1974 | Edwards | 260/302 R |

*Primary Examiner*—R. J. Gallagher
*Attorney, Agent, or Firm*—Gerard A. Blaufarb; Alan M. Krubiner

[57] ABSTRACT

1-Alkylamino-3-(5-alkynylaminocarbonylthiazol-2-yloxy)-2-propanol; 5-(5-alkynylaminocarbonyl-thiazol-2-yloxymethylene)-N-alkyloxazolidine and/or 2-substituted oxazolidine derivatives thereof, and methods of making such compounds. The compounds exhibit cardiovascular activity and are useful in the treatment of abnormal heart conditions in mammals. The compounds are also useful in the treatment of hypertension in mammals. The 5-(5-alkynyl-aminocarbonylthiazol-2-yloxymethylene)-N-alkyloxazolidines and derivatives are also intermediates for the 1-alkylamino-3-(5-alkynylaminocarbonylthiazol-2-yloxy)-2-propanols.

The 1-alkylamino-3-(5-alkynylaminocarbonylthiazol-2-yloxy)-2-propanols can be prepared by base or acid hydrolysis of the corresponding 5-(5-alkynylaminocarbonylthiazol-2-yloxymethylene)-N-alkyloxazolidine or derivative; or by treatment of the corresponding 3-(5-alkynylaminocarbonylthiazol-2-yloxy)-2,3-epoxypropane with the desired alkylamine. Similarly the 5-(5-alkynylaminocarbonylthiazol-2-yloxymethylene)-N-alkyloxazolidine or derivative can be prepared from the corresponding 1-alkylamino-3-(5-alkynylaminocarbonylthiazol-2-yloxy)-2-propanols via treatment with an aldehyde or ketone.

43 Claims, No Drawings

THIAZOLE CARDIOVASCULAR AGENTS

BACKGROUND OF THE INVENTION

1. Field of the Invention

This invention relates to 1-alkylamino-3-(5-alkynylaminocarbonylthiazol-2-yloxy)-propan-2-ol and pharmaceutically acceptable salts thereof; 5-(5-alkynylaminocarbonylthiazol-2-yloxymethylene)-N-alkyloxazolidine derivatives and pharmaceutically acceptable salts thereof and to method of preparing such compounds. In a further aspect this invention relates to pharmaceutical compositions comprising one or more of the above compounds, of the invention, and to methods of treating cardiac disorders and hypertension in mammals.

2. The Prior Art

At the present time, the compound frequently used in the United States for the treatment of several cardiac arrhythmias is propranolol (i.e. 1-(isopropylamino)-3-(1-naphthyloxy)-2-propanol). This compound primarily achieves its therapeutic action by blocking cardiac β-adrenergic receptor sites and is a general β-adrenergic blocker which blocks all β-adrenergic receptor sites including those in the lung, as well as the β-adrenergic receptor sites in the heart. Propanolol is contraindicated in patients who suffer from asthma or chronic obstructive lung disease, because following its administration to such patients, an increase in airway resistance and bronchial constriction has been observed. U.S. Pat. No. 3,897,441 discloses certain 3-(5-substituted aminocarbonylthiazol-2-yloxy)-propan-2-ol-1-amines having potent β-adrenergic blocking activity and cardiac selectivity. We have now discovered novel analogues of this class of compounds having unexpectedly superior β-blocking activity and/or cardiac selectivity and/or reduced cardiac depression. The compounds are especially felicitous for the treatment or palliation of angina pectoris and cardiac arrhythmias and because of their cardiac selectivity can be safely applied to patients who suffer from asthma or chronic obstructive lung disease.

SUMMARY OF THE INVENTION

In summary the compounds of the invention can be represented by the following generic formula:

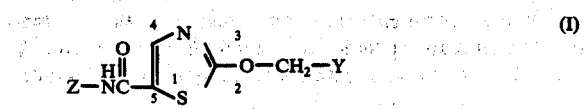

(I)

wherein
Z has the formula:

$R^1-C\equiv C-(CH_2)_n-$ wherein $n$ is 2, 3 or 4; $R^1$ is hydrogen or an alkyl group having from one through four carbon atoms and wherein Z has from four through eight carbon atoms;
Y is selected from the group having the formulas:

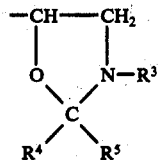

wherein $R^2$ and $R^3$ are lower alkyl; and $R^4$ and $R^5$ are independently hydrogen or lower alkyl.

Also encompassed within the invention are pharmaceutically acceptable salts of the above compounds.

In summary the process of the invention for preparing the compound, of the invention, wherein Y is the group $-CHOH-CH_2-NHR^2$ comprises treating the corresponding 3-(5-substituted thiazol-2-yloxy)-1,2-epoxypropane with an alkylamine having the desired $R^2$ substituent. Alternatively, these compounds can be prepared, according to the invention, by hydrolysis of the corresponding compounds of the invention, wherein Y is oxazolidine.

In summary the processes of the invention for preparing the compounds of the invention wherein Y is an oxazolidine group comprises condensing a 2-bromo or 2-chlorothiazole having the desired 5-position substituent with a 5-hydroxymethyl-oxazolidine having the desired $R^3$, $R^4$ and $R^5$-substituents or treating the corresponding compounds of the invention where Y is an alkylaminopropanol with the desired $R^4$, $R^5$ aldehyde or ketone.

In summary the pharmaceutical compositions of the invention include both solutions and solids or powders comprising one or more of the compounds, of the invention, in combination with a suitable pharmaceutical solution (e.g. sterile water) or pharmaceutical solid excipients.

The invention will be further described hereinbelow.

FURTHER DESCRIPTION OF THE INVENTION AND PREFERRED EMBODIMENTS

The compounds of the invention can be represented by the following subgeneric formulas:

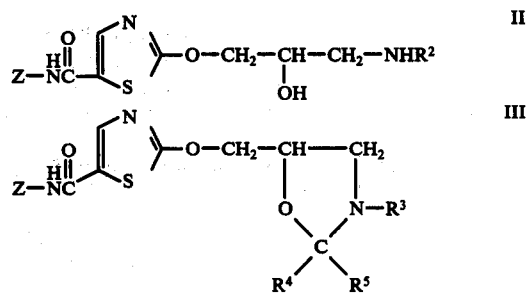

wherein
$R^2$ is lower alkyl group having from one through six carbon atoms and Z is a group having the formula

$R^1-C\equiv C-(CH_2)_n-$ wherein $n$ is 2, 3 or 4, and $R^1$ is hydrogen or an alkyl group having from one through four carbon atoms and wherein the total number of carbon atoms in Z is from four through eight;
$R^3$ is lower alkyl having one through six carbon atoms;

R[4] and R[5] are independently hydrogen or lower alkyl having from one through six carbon atoms, preferably hydrogen or methyl.

The pharmaceutically acceptable salts of the compounds of formulas II and III are also encompassed within the invention.

The above compounds have an asymmetric carbon atom in the propoxy side chain and hence exist as optical isomers. Further, where the R[1] substituent is also dissymmetric, further optical isomers exist with respect to this substituent. Accordingly, the above formulas are intended to represent both the respective individual isomers and mixtures thereof and the respective individual isomers as well as mixtures thereof are encompassed within the invention.

DEFINITIONS

As used hereinabove and below, the following terms shall have the following meanings unless expressly states to the contrary. The term alkyl refers to both straight and branched chain alkyl groups. The term lower alkyl refers to both straight and branched chain alkyl groups having a total of from one through six carbon atoms and thus includes primary, secondary, and tertiary alkyl groups. Typical lower alkyls include, for example, methyl, ethyl, n-propyl, isopropyl, n-butyl, t-butyl, n-hexyl and the like.

The term alkynyl refers to unsaturated alkyl groups having a triple bond (e.g. $CH_3C \equiv C(CH_2)_2-$) and includes both straight and branched chain alkynyl groups. Typical alkynyl groups include, for example, but-3-ynyl (i.e. $HC \equiv C(CH_2)_2-$); hex-4-ynyl (i.e. $CH_3C \equiv C(CH_2)_3-$); 5,5-dimethylhex-3-ynyl (i.e.

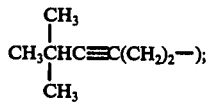

6-methylhept-4-ynyl (i.e.

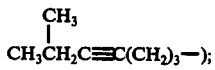

oct-5-ynyl (i.e. $C_2H_5C \equiv C(CH_2)_4-$) and the like.

The term alkylamino refers to the group having the formula R'HN— wherein R' is alkyl and the term lower alkylamino refers to such groups wherein R' is lower alkyl.

The term aminocarbonyl or carbamoyl refers to the group having the formula

The term alkynylaminocarbonyl or alkynylcarbamoyl refers to the group having the formula

wherein R[1] and n are as defined herein.

The term pharmaceutically acceptable salts refers to pharmaceutically acceptable hydrogen-anion addition salts which do not adversely affect the pharmaceutical properties of the parent compounds. With respect to the addition salts, suitable inorganic anions include, for example, chloride, bromide, iodide, sulfate, phosphate, nitrate, sulfate, and the like. Suitable organic anions include, for example, acetate, benzoate, lactate, picrate, propionate, butyrate, valerate, tartrate, maleate, fumarate, citrate, succinate, tosylate, ascorbate, nicotinate, adipate, gluconate and the like.

Typical illustrations of the compounds of formula II, and salts thereof, can be had, for example, hereinbelow by reference to Examples 1–4, 7 and 8. The preferred R[1] substituents are ethyl and isopropyl. The preferred R[2] substituent compounds of formula II are isopropyl and t-butyl and especially isopropyl. The preferred integer n is 2, i.e. ethyl. The particularly preferred compounds of formula II are:

1-isopropylamino-3-[5-(5-methylhex-3-ynylaminocarbonyl) thiazol-2-yloxy]-propan-2-ol;

1-t-butylamino-3-[5-(5-methylhex-3-ynylaminocarbonyl) thiazol-2-yloxy]-propan-2-ol;

1-isopropylamino-3-[5-(hex-3-ynylaminocarbonyl)-thiazol-2-yloxy]-propan-2-ol; and 1-t-butylamino-3-[5-(hex-3-ynylaminocarbonyl)-thiazol-2-yloxy]-propan-2-ol.

Typical illustrations of the compounds of formula III can be had, hereinbelow, by reference to Examples 5, 6 and 9. The preferred R[1] substituents and preferred n integers (i.e. 2) for the compounds of formula III are the same as listed above for the compounds as formula II. The preferred R[3] substituents are isopropyl and t-butyl. The simpler R[4] and R[5] substituents are preferred and hence the preferred compounds of formula III are those wherein R[4] and R[5] are each hydrogen or each methyl. The particularly preferred compounds of formula III are compounds having a preferred substituent at each of R[1], R[3], R[4] and R[5] and wherein n is 2, for example:

5-[5-(5-methylhex-3-ynylaminocarbonyl)thiazol-2-yloxy]methylene-N-isopropyl-2,2-dimethyloxazolidine;

5-[5-(5-methylhex-3-ynylaminocarbonyl)thiazol-2-yloxy]methylene-N-t-butyl-2,2-dimethyloxazolidine;

5-[5-(hex-3-ynylaminocarbonyl)thiazol-2-yloxy]-methylene-N-isopropyloxazolidine; and 5-[5-(hex-3-ynylaminocarbonyl)thiazol-2-yloxy]-methylene-N-t-butyl-2,2-dimethyloxazolidine.

The preferred pharmaceutically acceptable salts are hydrogen addition salts of chloride, bromide, sulfate, maleate, lactate, tartrate, succinate and especially chloride and maleate. Thus, the preferred salts are the preferred anion addition salts of formula II and III and correspondingly the particularly preferred salts are the preferred hydrogen-anion addition salts of the preferred and particularly preferred compounds of formulas II and III and especially the hydrochloride and maleate salts.

The compounds of formula II can be prepared by applying the procedures described in U.S. Pat. No. 3,891,441 (e.g. Col. 16, line 20–Col. 20, line 46 and Col. 27, line 34–Col. 30, line 39), which procedures are hereby incorporated by reference, to the corresponding 5-position substituted -2-bromo or -2-chloro thiazole substrate. These substrates can be prepared by applying the procedures described in Preparation 3, hereinbelow, to 2-bromo-5-carboxythiazole or 2-chloro-5-carboxythiazole.

The compounds of formula II can also be conveniently prepared by applying the simplified procedure described by Berkoz, Lewis and Muchowski in U.S. application Ser. No. 706,412, filed on even date herewith, to prepare the epoxy intermediate (B) and reacting this intermediate in accordance with the present invention with the appropriate alkylamine to obtain the desired compound of formula II. This procedure can be schematically represented by the following overall reaction sequence:

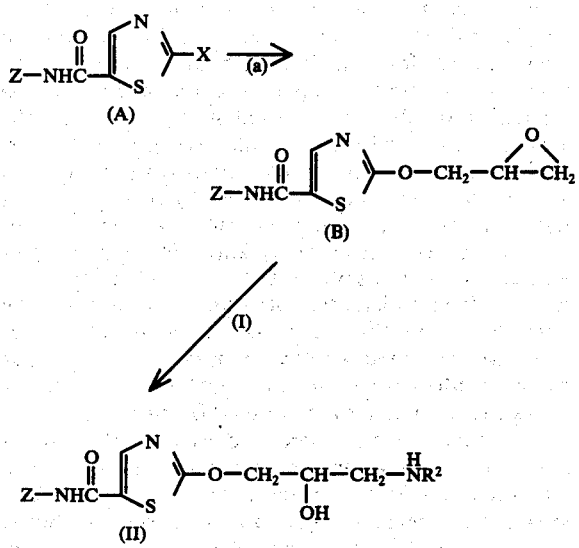

wherein X is chloro, bromo, $-SOR^6$ or $SO_2R^6$, wherein $R^6$ is methyl, ethyl or benzyl; and Z and $R^2$ are as defined hereinabove.

Procedure (a) can be effected by treating the compound of formula a with glycidol anion in an inert organic solvent. This treatment is conveniently conducted by first treating glycidol with an alkali metal hydride to generate the glycidol anion. This initial treatment is typically conducted at temperatures in the range of about from $-30°$ to $30°$ C, preferably about from $-10°$ to $5°$ C for about from 1 minute to 1 hour, preferably about from 5 minutes to 20 minutes. The compound of formula A, typically dissolved in an inert organic solvent, can then be treated with the preceding glycidol anion mixture. Typically, this treatment is conducted at temperatures in the range of about from $-30°$ to $25°$ C, preferably about from $-10°$ to $0°$ C, for about from 1 minute to 1 hour, preferably about from 10 to 30 minutes. Typically, mole ratios of alkali metal hydride to glycidol of about from 1 to 5 are used, preferably about from 1.0 to 1.3 , and mole ratios of compound of formula A to glycidol in the range of about from 1 to 5, preferably about from 1.0 to 1.3 are used. Suitable alkali metal hydrides which can be used include, for example, sodium hydride, potassium hydride, lithium hydride, and the like. Suitable inert organic solvents which can be used include, for example, tetrahydrofuran, diethyl ether, dioxane, dimethoxyethane, dimethylformamdide and the like, and mixtures thereof. Both procedures of the treatment are conducted under anhydrous conditions, and preferably under an inert atmosphere (e.g. nitrogen). The resulting product of formula B is preferably isolated before being used as starting material for the next step. Such isolation can be effected by conventional separation procedures such as, for example, precipitation with water, extraction, crystallization, or chromatography. Specific illustrations of typical separation and isolation procedures can be had by reference to the appropiate preparation, set forth hereinbelow.

The compounds of formula II can be conveniently prepared by treating the compound of formula B with a monoalkylamine having the desired alkyl substituent. Typically, this treatment is conducted in an inert organic solvent and is typically conducted at temperature in the range of about from $-10°$ to $100°$ C, preferably about from $10°$ to $25°$ C, for about from 1 hour to 48 hours, preferably about from 5 to 18 hours. Typically, a mole ratio of alkylamine to compound of formula B in the range of about from 1 to 30, preferably about from 1 to 10 is used. Suitable alkylamines which can be used include, for example, methylamine, ethylamine, isopropylamine, t-butylamine, n-pentylamine, 4-methylpentylamine, and the like. Suitable inert organic solvents which can be used include, for example, methanol, ethanol, monoglyme, acetone and the like and mixtures thereof. The resulting products of formula II can then be separated and isolated according to conventional procedures such as, for example, evaporation, crystallization, chromatography, thin-layer chromatography, etc. Specific illustrations of typical separation and isolation procedures can be had by reference to the corresponding examples, set forth hereinbelow.

The X is $-SOR^6$ and $-SO_2R^6$ starting materials of formula A can be prepared via the procedures described in Preparations A, B and 1–5 set forth hereinbelow or by obvious modifications thereof (for example, substitution of appropriate reagent such as, for example, methyl mercaptan or benzyl mercaptan for ethane thiol (i.e. ethyl mercaptan) in Preparation 1.

The compounds of formula III can be prepared by applying the procedures described in U.S. Pat. No. 3,897,441 , Col. 28, line 18–Col. 29, line 54, which procedures are hereby incorporated by reference, to the appropriate 2-bromo or

thiazole. As before noted, the appropriate 2-bromo or 2-chloro substrates can be prepared by applying the procedures described in Preparation 3, hereinbelow, to 2-bromo or 2-5-carboxythiazole.

The compounds of formula III can also be prepared directly from the corresponding compounds of formula II:

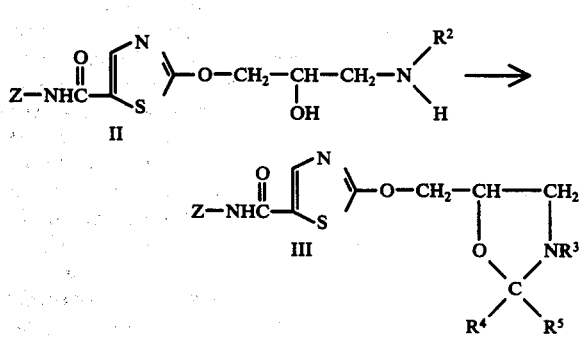

wherein $R^2$, $R^3$ and Z are as defined hereinabove.

This treatment can be convenienty effected by treating the corresponding compound of formula II with a ketone or aldehyde having the desired $R^4$ and $R^5$ substituents. Where a ketone is used, the reaction can be effected by treating the compound of formula II with the desired ketone and aluminum isopropoxide or aluminum t-butoxide. Typically a mole ratio of about from 1 to 10 moles of aluminum isopropoxide or aluminum t-butoxide and a substantial excess of ketone (e.g. 2 to 150 moles) which serves as solvent, are used per mole of compound of formula II. Where an aldehyde is used the reaction can be effected by simply treating the compound of formula II with the desired aldehyde using a lower alkanol (e.g. ethanol) as solvent. Typically a mole ratio of about from 1 to 10 moles of aldehyde is used per mole of formula II. In both cases the reaction are typically conducted at temperatures in the range of about from 20° to 100° C for about from 1 to 48 hours. Suitable ketones and aldehydes which can be used include, for example, formaldehyde, acetaldehyde, benzaldehyde, acetone, diethylketone, and the like.

The compounds of formula III can also be prepared via the procedure described in the said application Ser. No. 706,412 filed on even date herewith, and schematically represented hereinbelow.

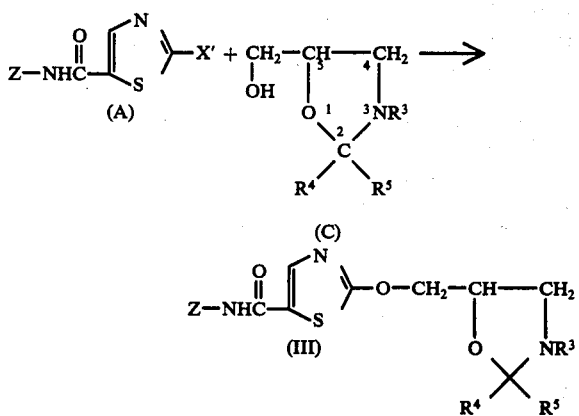

wherein $R^3$, $R^4$, $R^5$, and Z are as defined hereinabove, and X' is $-SOR^6$ or $-SO_2R^6$ wherein $R^6$ is methyl, ethyl or benzyl.

This procedure is preferably conducted in two steps. In the initial step the 5-hydroxymethyl-3-lower alkyl-oxazolidine or 2-mono or 2,2-dialkyl derivative thereof (formula C) is treated with an alkaline metal hydride, e.g. sodium hydride, in a suitable inert organic solvent. Typically, this treatment is conducted at temperatures in the range of about from $-5°$ to 100° C, preferably about from 25° to 60° C, for about from 10 minutes to 6 hours, preferably about from 1 to 3 hours. Suitable inert organic solvents which can be used include, for example, tetrahydrofuran, dimethylformamide, monoglyme, diglyme, and the like. The second step can be effected by treating the initial product reaction mixture with the desired 5-substituted-2-$SOR^6$ or 2—$SO_2R^6$ thiazole. Typically, this treatment is conducted at temperature in the range of about from $-20°$ to 80° C, preferably about from 0° to 30° C, for about from 1 minute to 10 hours, preferably about from 5 minutes to 2 hours. Typically, the thiazole reagent is added to the reaction mixture in the form of a solution in a suitable inert organic solvent. Suitable inert organic solvents which can be used include, for example, tetrahydrofuran, dimethylformamide, monoglyme, diglyme, and the like. Also, in some instances, an excess of the oxazolidine reagent can be used as the solvent. Both steps of this procedure are conducted under anhydrous conditions and preferably are conducted under an inert gas such as, for example, nitrogen.

The product of formula III can then be separated and purified according to conventional procedures such as, for example, illustrated in Example 6, hereinbelow. Care should be exercised during the purification procedure as the compounds of formula III are easily hydrolyzed to the compound of formula II under both acid and basic conditions. Correspondingly, the alkylamino compounds of formula II can be readily prepared by simple acid or base hydrolysis of the corresponding compounds of formula III. Acid hydrolysis can be conveniently effected by treating the compound of formula III with a suitable organic acid such as, for example, acetic, formic, oxalic acid and the like or suitable inorganic acid such as, for example, hydrochloric, sulfuric, and the like. Preferably this hydrolysis is conducted under mildly acidic conditions. Similarly, basic hydrolysis can be conducted by treating the compound of formula III with a suitable base such as, for example, dilute sodium hydroxide, potassium hydroxide and the like. Preferably this hydrolysis is conducted under mildly alkaline conditions. Alternatively, the hydrolysis can be conducted via exchange with a suitable ion exchange resin in either the H+ or OH− form.

Where desired the individual diastereomeric and optical isomers can be obtained; (1) by conventional separation and purification procedures in the case of diastereomeric isomers, and (2) via conventional resolution procedures in the case of optical isomers (for example, by reacting the optical isomer mixtures with an optically active acid which will yield a mixture of optical salts of the compounds of formula II which can be resolved by conventional procedures (e.g. crystallization) into the respective (+) and (−) optical salts. Optimum physical, or physical-chemical, separation procedures and resolution procedures can be obtained by routine trial and error procedures well within the scope of those skilled in the art. The specific optical isomers, or, in some instances, enriched optical isomer mixture, with respect to the propan-2-ol side chain (formula II) can also be prepared by applying the corresponding (+) or (−) optically active isomer of glycerol acetonide in the procedures referenced to U.S. Pat. No. 3,897,441, hereinabove on page 11, to a 2-bromo, 2-chloro, 2-ethylsulfinyl or 2-ethylsulfonyl 5-substituted thiazole starting material having the desired 5-position substituent. Where enriched isomer mixtures are obtained, the respective optical isomers can then be obtained by conventional resolution procedures.

The pharmaceutically acceptable acid addition salts of the compounds of formulas II and III can be prepared from the parent compound, via careful neutralization of the 1-alkylaminopropane moiety, with the desired acid. Other pharmaceutically acceptable addition salts can then be conveniently prepared from the addition salts via anion exchange with a suitable ion exchange resin in the desired anionic form.

The compounds, of the invention, are useful in the treatment and palliation of cardiovascular abnormalities in mammals. These compounds primarily achieve their therapeutic action by selectively blocking the cardiac β-adreneric receptor sites and, accordingly, because they are cardiac selective, they can also be applied to treat cardiac abnormalities in patients suffering from asthma or chronic obstructive lung disease. Further, based on the virtual identity of therapeutic activity, observed between the counterparts of formulas II and III, and the fact that the compounds of formula III are readily hydrolyzed to the compounds of formula II, it is believed that the compounds of formula III hydrolyze in vivo and hence function therapeutically as the compounds of formula II. The compounds are especially useful in the treatment or palliation of cardiac arrhythmias, angina pectoris, hypertrophic subaortic stenosis, pheochromocytoma, thyrotoxicosis, hyperkinetic syndromes, tetralogy of Fallot, mitral stenosis with tachycardia, general ischemic conditions, and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication (i.e. nitroglycerin) presently commonly used in the treatment of angina pectoris has no recognized prophylactic action. Additional information concerning the use, action and determination of β-blockers can be obtained by reference to the literature such as, for example, Dotlery, et al., *Clinical Pharmacology and Therapeutics*, volume 10, no. 6,765–797 and the references cited herein.

The compounds of the invention are also useful in the treatment of hypertension in mammals.

The compounds of this invention are typically administered, both for the treatment of cardiac disorders and hypertension, in dosages of about from 0.01 to 5 mg. per kg. of body weight. The precise effective dosage will, of course, vary depending upon the mode of administration, the condition being treated and the host. Where the compounds are used to treat cardiac conditions such as arrhythmias, the compounds are typically administered either orally or intravenously. Where the compounds are administered to treat hypertension or cardiac conditions such as angina pectoris, the compounds are, for the sake of convenience, typically administered orally.

The compounds of the invention can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. In the case of the compounds of formula II, the compounds are typically administered as pharmaceutically acceptable salts. The pharmaceutical carrier can be either a solid material or liquid, in which the compound is dissolved, dispersed or suspended, and can optionally contain small amounts of preservations and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs and optionally can contain small quantities of preservatives and/or buffering agents, and preferably contain the therapeutic agent in convenient unit dosage concentrations.

The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, sodium bisulfite and the like.

Also based on studies on related compounds, it can be predicted that a number of the present compounds will exhibit useful local anesthetic activity. Where the compounds are applied as local anesthetics, they can be administered topically; intradermally; or subcutaneously.

A further understanding of the invention can be held from the following non-limiting Preparations and Examples. Also as used hereinabove and below unless expressly stated to the contrary, all temperatures and temperature ranges refer to the Centrigrade system and the terms ambient or room temperature refer to about 20° C. The term percent or (%) refers to weight percent and the term mole or moles refers to gram moles. The term equivalent refers to a quantity of reagent equal in moles to the moles of the preceding or succeeding reactant recited in that Preparation or Example in terms of moles or finite weight or volume. Also unless expressly stated to the contrary, recemic mixtures and/or diastereomer mixtures are used as starting materials and correspondingly racemic mixtures and/or diastereomer mixtures are obtained as products and where necessary, preparations and examples are repeated to provide sufficient quantities of starting materials for subsequent preparations and examples.

PREPARATION A

Alkynylamines a. In this preparation 1.0 mole of p-toluenesulfonyl chloride is dissolved in 700 ml. of pyridine at 0° C, under nitrogen, and then 0.5 mole of hex-5-yn-1-ol is added dropwise. The mixture is stirred for 2 hours and then 10 ml. of water is added slowly, keeping the temperature below 10° C. The pyridine is then removed by evaporation under vacuum and the residue poured into 1 liter of ethyl acetate, then washed twice with excess 2N aqueous hydrochloric acid, and then with water. The organic layer is separated and dried over anhydrous magnesium sulfate, filtered, and the filtrate then evaporated to dryness, under vacuum, affording hex-5-yn-1-ol tosylate.

b. A mixture containing 0.397 mole of hex-5-yn-1-ol tosylate; 0.76 mole of sodium azide; and one liter of methanol and 200 ml. of water is stirred at 60° C for 4 hours. The mixture is then evaporated under vacuum to remove the majority of the methanol and the remaining concentrate then poured into 500 ml. of ethyl ether, and then extracted three times with water, and dried over anhydrous magnesium sulfate and filtered. The filtrate is then evaporated, under vacuum, affording 1-azidohex-5-yne as a residue.

c. 0.122 Mole of lithium aluminum hydride is dissolved in 500 ml. of ethyl ether, under nitrogen, and then 0.244 mole of 1-azidohex-5-yne in 100 ml. of diethyl ether is added dropwise. The mixture is then stirred at room temperature for 4 hours and then cooled to 0° C and 10 ml. of water carefully added and the mixture then filtered. The filtrate is then dried over potassium hydroxide pellets, filtered, and the filtrate distilled, affording 1-aminohex-5-yne as a residue.

Similarly, by following the same procedure as described above, but using the corresponding alkynyl-ols as starting materials in place of hex-5-yn-1-ol, in paragraph (a), the following alkynylamines are respectively prepared.
1-aminobut-3-yne;
1-aminopent-3-yne;
1-aminohex-3-yne;
1-aminohept-3-yne;
1-amino-5-methylhex-3-yne;
1-aminooct-2-yne;
1-amino-6-methylhept-3-yne;
1-aminopent-4-yne;
1-aminohex-4-yne;
1-aminohept-4-yne;
1-aminooct-4-yne;
1-amino-6-methylhept-4-yne;
1-aminohept-5-yne; and
1-aminooct-5-yne.

PREPARATION B

Alkynylamines a. This preparation illustrates further procedures for preparing alkynylamines. In this preparation 0.1 mole of 5,5-dimethylhex-3-yn-1-ol is mixed with 0.1 mole of triphenylphosphine in 40 ml. of carbon tetrachloride and then heated, under nitrogen, at 60° C for 4 hours. The mixture is then poured into 200 ml. of hexane, stirred, and then filtered and the filtrate concentrated by evaporation under vacuum. The concentrate is then chromatographed on silica gel eluting with 5% ethyl acetate-95% vol. hexane, affording 5,5-dimethylhex-3-yn-1-yl chloride. b. 0.069 Mole of 5,5-dimethylhex-3-yn-1-yl chloride is treated according to the procedures described in paragraph (b) of Preparation A, affording 1-azido-5,5-dimethylhex-3-yne. c. 0.069 Mole of 1-azido-5,5-dimethylhex-3-yne is treated according to the procedure described herein in paragraph (c) of Preparation A affording 1-amino-5,5-dimethylhex-3-yne.

Similarly by following the same procedure as described hereinabove by using the corresponding alkynyl-1-ol starting materials, the alkynylamines, prepared in Preparation A, are respectively prepared.

PREPARATION 1

2-Ethylthiothiazole

In this preparation 0.15 moles of 50% sodium hydride in mineral oil is stirred in 100 ml. of dimethylformamide, under a nitrogen atmosphere, then cooled to −50° C and 0.15 moles of ethanethiol is added dropwise. The resulting mixture is warmed to 0° C and then recooled to −50° C and 0.1 moles of 2-bromothiazole (K. Ganapthi et al., *Proc. Indian Acad. Sci.*, A22, 362 (1945) is added. The resulting mixture is warmed to room temperature (about 20° C) and maintained at this temperature until the reaction is determined to be complete as shown by thin-layer chromatography; about two hours. The mixture is then poured into 500 ml. of hexane, then washed three times with water. The organic layer is dried with anhydrous magnesium sulfate, filtered, and the resulting filtrate evaporated under vacuum yielding 2-ethylthiothiazole as a colorless oil.

PREPARATION 2

2-Ethylthio-5-carboxythiazole

In this preparation 0.2 moles of 2-ethylthiothiazole is dissolved in 300 ml. of anhydrous tetrahydrofuran, under a nitrogen atmosphere, then cooled to −80° C. 0.2 Moles of butyl lithium in 125 ml. of hexane is then added dropwise with stirring. The mixture is stirred for 5 minutes and then anhydrous carbon dioxide bubbled through the mixture until reaction is completed (the reaction is monitored by thin-layer chromatography). The mixture is allowed to warm to 0° C, 300 ml. of hexane added, and then filtered. The filter cake is recovered and washed with ethyl ether, affording the lithium salt of 2-ethylthio-5-carboxythiazole, and then slurried with 300 ml. of ethyl acetate. The ethyl acetate slurry is then acidified with 2 Normal hydrochloric acid and washed with water. The organic layer is recovered, dried with anhydrous magnesium sulfate, and the resulting filtrate evaporated to dryness under vacuum yielding 2-ethylthio-5-carboxythiazole.

PREPARATION 3

2-Alkylthio-5-alkynylaminocarbonylthiazole

In this preparation 0.1 mole of 2-ethylthio-5-carboxythiazole is dissolved in 300 ml. of anhydrous tetrahydrofuran, under nitrogen, and 0.1 moles of triethylamine is added and the resulting mixture cooled to −30° C. 0.1 Mole of ethylchloroformate is then added dropwise with stirring and the resulting mixture allowed to warm to 0° C. The mixture is then stirred for ten minutes, then cooled to −30° C and 0.11 mole of 1-aminohex-5-yne in 50 ml. of tetrahydrofuran added dropwise. The mixture is allowed to warm to room temperature (about 20° C), poured into 500 ml. of ethyl acetate, washed with water, then washed with saturated aqueous sodium chloride solution, and dried over magnesium sulfate. The mixture is then filtered and the solvent from the resulting filtrate is evaporated under vacuum yielding 2-ethylthio-5-(hex-5-ynylaminocarbonyl)thiazole as a solid, which is then further purified by recrystallization from ethyl acetate.

Similarly, by following the same procedure but respectively using the corresponding aminoalkyne products of Preparations A and B hereinabove, in place of 1-aminohex-5-yne, the following compounds are respectively prepared:
2-ethylthio-5-(but-3-ynylaminocarbonyl)thiazole;
2-ethylthio-5-(pent-3-ynylaminocarbonyl)thiazole;
2-ethylthio-5-(hex-3-ynylaminocarbonyl)thiazole;
2-ethylthio-5-(hept-3-ynylaminocarbonyl)thiazole;
2-ethylthio-5-(5-methylhex-3-ynylaminocarbonyl)thiazole;
2-ethylthio-5-(5,5-dimethylhex-3-ynylaminocarbonyl)thiazole;
2-ethylthio-5-(pent-4-ynylaminocarbonyl)thiazole;
2-ethylthio-5-(hex-4-ynylaminocarbonyl)thiazole;
2-ethylthio-5-(hept-4-ynylaminocarbonyl)thiazole;
2-ethylthio-5-(oct-4-ynylaminocarbonyl)thiazole;
2-ethylthio-5-(6-methylhept-4-ynylaminocarbonyl)thiazole;
2-ethylthio-5-(hept-5-ynylaminocarbonyl)thiazole; and
2-ethylthio-5-(oct-5-ynylaminocarbonyl)thiazole.

PREPARATION 4

2-Ethylsulfinyl-5-alkynylaminocarbonylthiazole

In this preparation a mixture of 0.064 mole of 2-ethylthio-5-(hex-5-ynylaminocarbonyl) thiazole; 40 ml. of 30% aqueous hydrogen peroxide and 200 ml. of acetic acid is stirred at a temperature of from 40° to 50° C for 4 hours. The mixture is concentrated by evaporation of a large portion of the acetic acid, under vacuum, at room temperature (about 20° C) and the resulting residue poured into 500 ml. of ethyl acetate and then washed with aqueous sodium bicarbonate solution until no acetic acid is present in the organic layer. The ethyl acetate layer is then separated, dried with anhydrous magnesium sulfate, filtered, and the resulting filtrate evaporated to dryness, under vacuum, affording 2-ethylsulfinyl-5-(hex-5-ynylaminocarbonyl)thiazole.

Similarly, by following the same procedure but respectively replacing 2-ethylthio-5-(hex-5-ynylaminocarbonyl)thiazole with the products of Preparation 3, the corresponding 2-ethylsulfinyl analogs are respectively prepared.

PREPARATION 5

2-Ethylsulfonyl-5-alkynylaminocarbonylthiazole

In this preparation a mixture of 0.028 mole of 2-ethylthio-5-(5-methylhex-3-ynylaminocarbonyl)-thiazole; 20 ml. of 30% hydrogen peroxide and 100 ml. of acetic acid are heated at 55° C for 16 hours, most of the acetic acid is then removed by evaporation under vacuum and the resulting residue dissolved in 250 ml. of ethyl acetate and then washed with aqueous sodium bicarbonate solution until all traces of acetic acid are removed. The ethyl acetate layer is separated and then dried with anhydrous magnesium sulfate, filtered, and the resulting filtrate evaporated under vacuum to dryness affording 2-ethylsulfonyl-5-(5-methylhex-3-ynylaminocarbonyl)thiazole.

Similarly, by following the same procedure but respectively replacing 2-ethylthio-5-(5-methylhex-3-ynylaminocarbonyl)thiazol with the products of Preparation 3, the corresponding 2-ethylsulfonyl analogs are respectively prepared.

PREPARATION 6

1,2Epoxy-3-(5-alkynylaminocarbonylthiazol-2-yloxy)propane

In this preparation 0.0525 mole of sodium hydride in a 50% mineral oil mixture is stirred in 300 ml. of anhydrous tetrahydrofuran, under nitrogen, then cooled to −30° C and 0.055 mole glycidol is added dropwise. The mixture is allowed to warm −5° C and stirred for 10 minutes and then recooled to −30° C. A solution of 0.05 mole of 2-ethylsulfinyl-5-(hex-5-ynylaminocarbonyl)-thiazole in 100 ml. of anhydrous tetradrofuran is added dropwise and the resulting solvent is added as needed to facilitate stirring. The mixture is maintained for 30 minutes at 0° C and then poured into 500 ml. of ethyl acetate, extracted with 100 ml. of water, and then with 100 ml. of aqueous saturated sodium chloride and dried over anhydrous magnesium sulfate and filtered. The filtrate is evaporated under vacuum affording an oily residue which is then further purified by chromatography on silica gel eluting with 40% ethyl acetate-60% hexane, by vol., affording 1,2-epoxy-3-[5-(hex-5-ynylaminocarbonyl)thiazol-2-yloxy]propane.

Similarly, by following the same procedure, the products of Preparation 4 are respectively converted into the corresponding 1,2-epoxy analogs.

PREPARATION 7

1,2-Epoxy-3-(5-alkynylaminocarbonylthiazol-2-yloxy)propane

In this preparation 0.0525 mole of sodium hydride in a 50% mineral oil mixture is stirred in 300 ml. of anhydrous tetrahydrofuran, under nitrogen, then cooled to −30° C and 0.055 mole of glycidol is added dropwise. The mixture is allowed to warm to −5° C and stirred for 10 minutes and then recooled to −30° C. A solution of 0.05 mole of 2-ethylsulfonyl-5-(5-methylhex-3-ynylaminocarbonyl)thiazole in 100 ml. of anhydrous tetrahydrofuran is added dropwise and the resulting mixture allowed to warm to 0° C. Additional solvent is added as needed to facilitate stirring. The mixture is maintained at 30 minutes at 0° C and then poured into 500 ml. of ethyl acetate, extracted with 100 ml. of water, and then with 100 ml. of aqueous saturated sodium chloride and dried over anhydrous magnesium sulfate and filtered. The filtrate is evaporated under vacuum affording an oily residue which is then further purified by chromatography on silica gel eluting with 40% ethyl acetate-60% hexane, by vol., affording 1,2-epoxy-3-[5-(5-methylhex-3-ynylaminocarbonyl)thiazol-2-yloxy]-propane.

Similarly, by following the same procedure, the products of Preparation 5 are respectively converted into the corresponding 1,2-epoxy analogs.

PREPARATION 8

In this example sodium hydride (18 g., 56 wt. % dispersion in oil) is washed with n-hexane, and the hexane is replaced with monoglyme (100 ml.). To this mixture is added a solution of 44.5 g. of (+) glycerol acetonide (*J. Biol. Chem.*, v. 128, page 463 (1939) in monoglyme (200 ml.) under an atmosphere of nitrogen. After 15 minutes, 2-ethylsulfonyl-5-(hex-5-ynylaminocarbonyl)thiazole (32 g.) is added, and the mixture is refluxed for 1 hour. The reaction mixture is then cooled, diluted with ethyl ether, washed with saturated aqueous sodium chloride solution twice, dried and concentrated by evaporation. Column chromatography, eluting with ethyl acetate/hexane (1:1), yields (+) 3-[5-(hex-5-ynylaminocarbonyl)thiazol-2-yloxy]propanediol 1,2-acetonide.

Similarly, by following the same procedure but respectively replacing 2-ethylsulfonyl-5-(hex-5-ynylaminocarbonyl) thiazole with the compounds prepared in Preparations 4 and 5, the corresponding (+) 3-(5-alkynylaminocarbonylthiazol-2-yloxy)-propanediol 1,2-acetonide compounds are respectively prepared.

Similarly, the above procedure is respectively repeated with each of the above 2-ethylsulfinyl and 2-ethylsulfonyl starting materials but using (−) glycerol acetonide (*J. Am. Chem. Soc.*, v. 67, page 944 (1945)) in place of (+) glycerol acetonide to yield the corresponding (−) 3-(5-alkynylaminocarbonylthiazol-2-yloxy)-propanediol 1,2-acetonide.

PREPARATION 9

In this example a mixture containing 2 g. of (+) 3-[5-(hex-5-ynylaminocarbonyl)thiazol-2-yloxy]propanediol 1,2-acetonide in 25 ml. of 80% aqueous formic acid is stirred at room temperature for 5 minutes. The solution is then evaporated under vacuum at room temperature affording a residue of (+) 3-[5-(hex-5-ynylaminocarbonyl)thiazol-2-yloxy]propane-1,2-diol which is then further purified by recrystallization using an ethyl acetate-hexane mixture.

Similarly, by following the same procedure, the products prepared according to Preparation 8 are respectively cleaved to the corresponding optically active propanediol compounds.

PREPARATION 10

In this example 0.42 g. of methanesulfonyl chloride is added with rapid stirring to a mixture containing 1.2 g. of (+) 3-[5-(hex-5-ynylaminocarbonyl)thiazol-2-yloxy]-propane-1,2-diol in 20 ml. of pyridine at −30° C. The mixture is then allowed to warm to room temperature and evaporated to dryness affording a residue of (+) 2-hydroxy-1-methylsulfonyloxy-3-(5(-hex-5-ynylaminocarbonyl)thiazol-2-yloxy]propane. The residue is then dissolved in 50 ml. of anhydrous methanol and cooled to 0° C. A mixture containing 1 g. of sodium methoxide in 10 ml. of anhydrous methanol is added and the resulting mixture stirred for 2 minutes and then evaporated to remove methanol. 100 Ml. of ethyl acetate is added and the resulting ethyl acetate mixture washed three times with water, dried over magnesium sulfate, and evaporated affording a residue of (+) 1,2-epoxy-3-[5-(hex-5-ynylaminocarbonyl)thiazol-2-yloxy]propane.

Similarly, by following the same procedure as above, the products of Preparation 9 are respectively converted to the corresponding optically active 1,2-epoxy-propane-5-substituted alkylaminocarbonylthiazole derivatives.

EXAMPLE 1

This examole illustrates methods for preparing the compounds of the present invention. In this examole a mixture containing 12 g. (0.037 mole) of 1,2-epoxy-3-[5-(hex-5-ynylaminocarbonyl)thiazol-2-yloxy]propane, 12 g. (0.164 mole) of t-butylamine and 20 ml. of ethanol is allowed to stand at room temperature for 12 hours. The mixture is then evaporated under vacuum to remove the ethanol solvent and the resulting residue dissolved in 50 ml. of ethyl acetate and cooled to −20° C, and maintained at this temperature for two hours. The mixture is then filtered and the resulting filter cake washed with cold (about 0° C) ethyl ether and then recrystallized from ethyl acetate affording 1-t-butylamino-3-[5-(hex-5-ynylaminocarbonyl)thiazol-2-yloxy]propan-2-ol, m.p. 140°–148° C.

Similarly, by following the same procedure but using the corresponding products of Preparation 6 as starting materials, the following compounds are respectively prepared.

1-t-butylamino-3-[5-(but-3-ynylaminocarbonyl)-thiazol-2-yloxy]-propan-2-ol;
1-t-butylamino-3-[5-(pent-3-ynylaminocarbonyl)-thiazol-2-yloxy]-propan-2-ol;
1-t-butylamino-3-[5-(hex-3-ynylaminocarbonyl)-thiazol-2-yloxy]-2-ol, m.p. 90°–91° C;
1-t-butylamino-3-[5-(hept-3-ynylaminocarbonyl)-thiazol-2-yloxy]-propan-2-ol;
1-t-butylamino-3-[5-(5-methylhex-3-ynylaminocarbonyl) thiazol-2-yloxy]-propan-2-ol;
1-t-butylamino-3-[5-(oct-3-ynylaminocarbonyl)-thiazol-2-yloxy]-propan-2-ol;
1-t-butylamino-3-[5-(6-methylhept-3-ynylaminocarbonyl) thiazol-2-yloxy]-propan-2-ol;
1-t-butylamino-3-[5-(5,5-dimethylhex-3-ynylaminocarbonyl)-thiazol-2-yloxy]-propan-2-ol;
1-t-butylamino-3-[5-pent-4-ynylaminocarbonyl)-thiazol-2-yloxy]-propan-2-ol;
1-t-butylamino-3-[5-(hex-4-ynylaminocarbonyl)-thiazol-2-yloxy]-propan-2-ol;
1-t-butylamino-3-[5-(hept-4-ynylaminocarbonyl)-thiazol-2-yloxy]-propan-2-ol;
1-t-butylamino-3-[5-(6-methylhept-4-ynylaminocarbonyl)thiazol-2-yloxy]-propan-2-ol;
1-t-butylamino-3-[5-(hept-5-ynylaminocarbonyl)-thiazol-2-yloxy]-propan-2-ol; and
1-t-butylamino-3-[5-oct-5-ynylaminocarbonyl)-thiazol-2-yloxy]-propan-2-ol.

Similarly, by following the same procedure but replacing t-butylamine with methylamine and hexylamine, the corresponding methylamino and hexylamino homologs of the above products are respectively prepared.

Similarly, by following the same procedure but using the products of Preparation 10 as starting materials, the corresponding (+) and (−) optically active (relative to the propan-2-ol side chain) isomers of each of the above products is respectively prepared.

EXAMPLE 2

This example illustrates methods for preparing the compounds of the present invention. In this example a mixture containing 12 g. (0.0314 mole) of 1,2-epoxy-3-[5-(5-methylhex-3-ynylaminocarbonyl)thiazol-2-yloxy]-propane, 12 g. (0.203 mole) of isopropylamine and 20 ml. of ethanol is allowed to stand at room temperature for 12 hours. The mixture is then evaporated under vacuum to remove the solvent and the resulting residue dissolved in 50 ml. of ethyl acetate and cooled to −20° C, and maintained at this temperature for 2 hours. The mixture is then filtered and the resulting filter cake washed with cold (about 0° C) ethyl ether and then recrystallized from ethyl acetate affording 1-iso-propylamino-3-[5-(5-methylhex-3-ynylaminocarbonyl)-thiazol-2-yloxy]-propan-2-ol.

Similarly, by following the same procedure but using the corresponding products of Preparation 7 as starting materials, the following compounds are respectively prepared:

1-ispropylamino-3-[5-(but-3-ynylaminocarbonyl)-thiazol-2-yloxy]-propan-2-ol;
1-isopropylamino-3-[5-(pent-3-ynylaminocarbonyl)-thiazol-2-yloxy]-propan-2-ol;
1-isopropylamino-3-[5-(hex-3-ynylaminocarbonyl)-thiazol-2-yloxy]-propan-2-ol;
1-isopropylamino-3-[5-(hept-3-ynylaminocarbonyl)-thiazol-2-yloxy]-propan-2-ol;
1-isopropylamino-3-[5-(oct-3-ynylaminocarbonyl)-thiazol-2-yloxy]-propan-2-ol;
1-isopropylamino-3-[5-(6-methylhept-3-ynylaminocarbonyl)thiazol-2-yloxy]-propan-2-ol;
1-isopropylamino-3-[5-(5,5-dimethylhex-3-ynylaminocarbonyl)thiazol-2-yloxy]-propan-2-ol;
1-isopropylamino-3-]5-(pent-4-ynylaminocarbonyl)-thiazol--yloxy]-propan-2-ol;
1-isopropylamino-3-[5-hex-4-ynylaminocarbonyl)-thiazol-2-yloxy]-propan-2-ol;
1-isopropylamino-3-[5-(hept-4-ynylaminocarbonyl)-thiazol-2-yloxy]-propan-2-ol;
1-isopropylamino-3-[5-(hex-5-ynylaminocarbonyl)-thiazol-2-yloxy]-propan-2-ol;
1-isopropylamino-3-]5(hept-5-ynylaminocarbonyl)-thiazol-2-yloxy]-propan-2-ol; and
1-isopropylamino-3-[-(oct-5-ynylaminocarbonyl)-thiazol-2-yloxy]-propan-2-ol.

Similarly, by following the same procedure but replacing isopropylamine with ethylamine and and pentylamine, the corresponding ethylamino and pentylamino homologs of the above products are respectively prepared.

Similarly, by following the same procedure but using the products of Preparation 10 as starting materials, the corresponding (+) and (−) optically active (relative to the propan-2-ol side chain) isomers of each of the above products is respectively prepared.

EXAMPLE 3

This example illustrates methods of preparing hydrochloride addition salts of the compounds of formula II. In this example 1 g. of 1-t-butylamino-3-[5-(hex-5-ynylaminocarbonyl)thiazol-2-yloxy]-propan-2-ol is dissolved in 10 ml. of ethyl ether at 20° C. A stream of gaseous anhydrous hydrogen chloride is passed over the surface of the solution until the supernatent liquid becomes clear. The resulting precipitate is collected by filtration, washed with ethyl ether and then crystallized from methanol/diethyl ether, affording crystalline 1-t-butylamino-3-[5-(hex-5-ynylaminocarbonyl) thiazol-2-yloxy]-propan-2-ol hydrochloride.

Similarly, by following the same procedure, the corresponding hydrochloride addition salts of each of the products of Examples 1 and 2 are respectively prepared, for example:

1-isopropylamino-3-[5-(hex-5-ynylaminocarbonyl)-thiazol-2-yloxy]-propan-2-ol hydrochloride.

EXAMPLE 4

This example illustrates methods of preparing the maleate addition salts of compounds of formula II. In this example 1 gram of 1-t-butylamino-3-[5-(5-methylhex-3-ynylaminocarbonyl)thiazol-2-yloxy]-propan-2-ol is dissolved in a solution of 5 ml. of ethyl ether and 5 ml. of ethanol at 20° C. To this solution is added 10 ml. of a saturated solution of maleic acid is ethyl ether. The mixture is allowed to stand for one hour at room temperature. The resulting precipitate is recovered by filtration, washed three times with ethyl ether and then crystallized from a mixture of ethyl ether and ethanol (1:1) affording crystalline 1-t-butylamino-3-[5-(5-methylhex-3-ynylaminocarbonyl)thiazol-2-yloxy]-propan-2-ol maleate, m.p. 174°–175° C.

Similarly, by following the same procedure, the corresponding maleate salts of each of the products of Examples 1 and 2 are respectively prepared, for example:

1-isopropylamino-3-[5-(5-methylhex-3-ynylaminocarbonyl) thiazol-2-yloxy]-propan-2-ol maleate, m.p. 152°–153° C.

EXAMPLE 5

This example illustrates methods of converting the corresponding $R^2$ compounds of formula II into the corresponding compounds of formula III of the invention. In this example, 1 g. of 1-isopropylamino-3-[5-(5-methylhex-3-ynylaminocarbonyl)thiazol-2-yloxy]-propan-2-ol is dissolved in 25 ml. of acetone at 20° C, and 2 g. of aluminum isopropoxide is then added. The solution is stirred for 4 days at 20° C and then 50 ml. of ethyl ether and 5 ml. of water are added and the resulting mixture is allowed to stand for 15 minutes. The resulting ethyl ether phase is separated and then evaporated to dryness yielding 5-[5-(5-methylhex-3-ynylaminocarbonyl)thiazol-2-yloxy]-methylene-N-isopropyl-2,2-dimethyloxazolidine.

Similarly, by following the same procedure, products of Examples 1 and 2 are respectively converted into the corresponding compounds of formula III.

EXAMPLE 6

This examples illustrates the preparation of the compounds of formula III, via the procedure described in the Application of Berkoz, Lewis and Muchowski, Ser. No. 706,412, filed on even date herewith. In this example 0.012 mole of sodium hydride (50% mineral oil) is stirred in 50 ml. of tetrahydrofuran; under nitrogen, and 0.02 mole of 5-hydroxymethyl-N-t-butyloxazolidine is added. The mixture is then warmed to 50° C until reaction ceases (about 30 minutes) and then cooled to room temperature. 0.01 Mole of 2-ethylsulfinyl-5-(hex-5-ynylaminocarbonyl)thiazole in 50 ml. of tetrahydrofuran is then added. The mixture is stirred for 4 hours at room temperature and then poured into 200 ml. of ethyl acetate, then washed with water; dried over anhydrous magnesium sulfate and filtered. The filtrate is evaporated under vacuum affording a crude 5-[5-(hex-5-ynylaminocarbonyl)thiazol-2-yloxy]-methylene-N-t-butyloxazolidine residue which is then dissolved in 100 ml. of diethyl ether and then hydrochloric acid gas is passed over the surface with rapid stirring until no more precipitate is formed. The precipitate is filtered off, washed with diethyl ether, and then recrystallized from a mixture of propanol and diethyl ether. The crystals are collected by filtration and dried under vacuum affording 5-[5-(hex-5-ynylaminocarbonyl)thiazol-2-yloxy]-methylene-N-t-butyloxazolidine hydrochloride.

Similarly, by following the same procedure but using the products of Preparation 4 as starting materials, the corresponding compounds of formula III and their hydrochloride salts are respectively prepared.

Similarly, by following the same procedure but respectively using the 2-ethylsulfonyl products of Preparation 5 as starting materials, the corresponding compounds of formula III and their hydrochloride salts are respectively prepared.

EXAMPLE 7

This example illustrates methods of converting the compounds of formula III into the compounds of formula II of the invention. In this example 1 g. of 5[5-(hex-5-ynylaminocarbonyl)thiazol-2-yloxy]-methylene-N-t-butyl-2,2-dimethyloxazolidine is dissolved in 50 ml. of tetrahydrofuran and this solution is treated with aqueous 5% sodium hydroxide (20 ml.) at 20° C. The mixture is stirred for 0.5 hour, extracted three times with methylene chloride, washed with water, dried over magnesium sulfate and then evaporated to dryness affording 1-t-butyl-3-[5-(hex-5-ynylaminocarbonyl)-thiazol-2-yloxy]-propan-2-ol.

Similarly, by following the same procedure, the products of Example 6 are respectively hydrolyzed to the corresponding compounds of formula II.

EXAMPLE 8

This example illustrates an alternate method for converting the compounds of formula III to the compounds of formula II. In this example 1 g. of 5-[5-(5-methylhex-3-ynylaminocarbonyl)thiazol-2-yloxy]-methylene-N-t-butyloxazolidine is dissolved in 20 ml. of methanol containing 4 cc. of 5% aqueous hydrochloric acid at 20° C. After 15 minutes, the mixture is neutralized with dilute aqueous sodium carbonate solution, poured into water and extracted with ethyl acetate. The ethyl acetate extract is evaporated to dryness yielding 1-t-butylamino-3-[5-(5-methylhex-3-ynylaminocarbonyl)-thiazol-2-yloxy]-propan-2-ol.

Similarly, by following the same procedure, the products of Example 6 are respectively hydrolyzed to the corresponding compounds of formula II.

EXAMPLE 9

This example illustrates further methods of converting the compounds of formula II into the corresponding compounds of formula III. In this example 1 m. mole of 1-isopropylamino-3-[5-(5-methylhex-3-ynylaminocarbonyl)thiazol-2-yloxy]-propan-2-ol in 10 ml. of methanol is admixed with 20 ml. of 37% aqueous formaldehyde and then stirred at room temperature for 1 hour. The solvent is then removed by evaporation under vacuum affording a crude 5-[5-(5-methylhex-3-ynylaminocarbonyl)thiazol-2-yloxy]-methylene-N-isopropyloxazolidine residue which is then stirred in 50 ml. of ethyl ether and filtered. Gaseous hydrogen chloride is passed over the surface of the filtrate with rapid stirring until no further precipitate is formed. The precipitate is filtered off, washed with diethyl ether and then recrystallized from a mixture of propanol and diethyl ether affording 5-[5-(5-methylhex-3-ynylaminocarbonyl)thiazol-2-yloxy]-methylene-N-isopropyloxazolidine hydrochloride.

Similarly, by following the same procedure, the products of Examples 1 and 2 are respectively converted to the corresponding compounds of formula III and their hydrochloride salts.

Similarly by following the same procedure but using acetaldehyde in place of formaldehyde, the corresponding 2-methyloxazolidine homologs of the above products are respectively prepared.

Obviously many modifications and variations of the invention, described herein above and below in the Claims, can be made without departing from the essence and scope thereof.

What is claimed is:

1. A compound selected from the group having the formula:

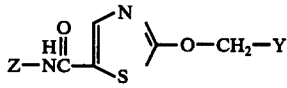

wherein
Z has the formula:

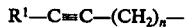

wherein $n$ is 2, 3 or 4; $R^1$ is hydrogen or an alkyl group having from one through four carbon atoms; and wherein Z has from four through eight carbon atoms;
Y is selected from the group having the formulas:

—CHOH—CH$_2$NHR$^2$;

or

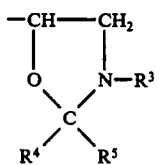

wherein $R^2$ and $R^3$ are lower alkyl and $R^4$ and $R^5$ are independently selected from the group of hydrogen or lower alkyl;
and pharmaceutically acceptable salts thereof.

2. The compound of claim 1 selected from the group having the formula:

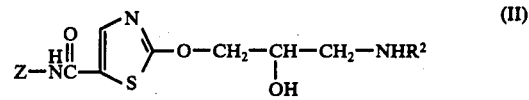

wherein $R^2$ is lower alkyl and Z has the formula

wherein $n$ is 2, 3 or 4; $R^1$ is hydrogen or an alkyl group having from one through four carbon atoms and wherein Z has from four through eight carbon atoms;
and pharmaceutically acceptable salts thereof.

3. The compound of claim 2 wherein $n$ is 2.
4. The compound of claim 2 wherein $R^2$ is selected from the group of isopropyl and t-butyl.
5. The compound of claim 2 wherein $R^2$ is isopropyl.
6. The compound of claim 2 wherein $n$ is 2 and $R^1$ is ethyl or isopropyl.
7. The compound of claim 6 wherein $R^2$ is isopropyl or t-butyl.
8. The compound of claim 7 wherein said compound is selected from the group consisting of 1-isopropylamino-3-[5-(5-methylhex-3-ynylaminocarbonyl)-thiazol-2-yloxyl-propan-2-ol and pharmaceutically acceptable salts thereof.
9. The compound of claim 7 wherein said compound is selected from the group consisting of 1-t-butylamino-3-[5-(5-methylhex-3-ynylaminocarbonyl)thiazol-2-yloxy]-propan-2-ol and pharmaceutically acceptable salts thereof.
10. The compound of claim 7 wherein said compound is selected from the group consisting of 1-isopropylamino-3-[5-(hex-3-ynylaminocarbonyl)thiazol-2-yloxy]-propan-2-ol and pharmaceutically acceptable salts thereof.
11. The compound of claim 7 wherein said compound is selected from the group consisting of 1-t-butylamino-3-[5-(hex-3-ynylaminocarbonyl)thiazol-2-yloxy]-propan-2-ol and pharmaceutically acceptable salts thereof.
12. The compound of claim 2 wherein $n$ is 3.
13. The compound of claim 12 wherein $R^1$ is methyl or ethyl.
14. The compound of claim 12 wherein $R^2$ is isopropyl or t-butyl.
15. The compound of claim 14 wherein $R^1$ is methyl.
16. The compound of claim 14 wherein $R^1$ is ethyl.
17. The compound of claim 2 wherein $n$ is 4.
18. The compound of claim 17 wherein $R^1$ is hydrogen or methyl.
19. The compound of claim 17 wherein $R^2$ is isopropyl or t-butyl.
20. The compound of claim 19 wherein $R^1$ is hydrogen.
21. The compound of claim 19 wherein $R^1$ is methyl.
22. The compound of claim 1 selected from the group having the formula:

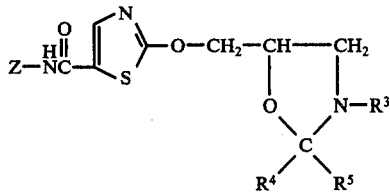

wherein
n is 2, 3 or 4; Z has the formula:

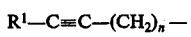

wherein $R^1$ is hydrogen or an alkyl group having from one through four carbon atoms and wherein Z has from four through eight carbon atoms:

$R^3$ is lower alkyl; and $R^4$ and $R^5$ are independently selected from the group of hydrogen and lower alkyl;

and pharmaceutically acceptable salts thereof.

23. The compound of claim 22 wherein n is 2.

24. The compound of claim 22 wherein $R^4$ and $R^5$ are independently selected from the group of hydrogen and methyl.

25. The compound of claim 22 wherein n is 2; $R^1$ is ethyl or isopropyl and $R^3$ is isopropyl or t-butyl.

26. The compound of claim 25 wherein $R^4$ and $R^5$ are each hydrogen or are each methyl.

27. The compound of claim 22 wherein n is 3, $R^1$ is methyl or ethyl, and $R^3$ is isopropyl or t-butyl.

28. The compound of claim 27 wherein $R^4$ and $R^5$ are each hydrogen or are each methyl.

29. The compound of claim 22 wherein n is 4, $R^1$ is hydrogen or methyl and $R^3$ is isopropyl or t-butyl.

30. The compound of claim 29 wherein $R^4$ and $R^5$ are each hydrogen or are each methyl.

31. The compound of claim 2 wherein when said compound is a pharmaceutically acceptable salt said salt is selected from the group consisting of hydrochloride and maleate salts.

32. The compound of claim 8 wherein when said compound is a pharmaceutically acceptable salt said salt is selected from the group consisting of hydrochloride and maleate salts.

33. The compound of claim 9 wherein when said compound is a pharmaceutically acceptable salt said salt is selected from the group consisting of hydrochloride and maleate salts.

34. The compound of claim 10 wherein when said compound is a pharmaceutically acceptable salt said salt is selected from the group consisting of hydrochloride and maleate salts.

35. The compound of claim 11 wherein when said compound is a pharmaceutically acceptable salt said salt is selected from the group consisting of hydrochloride and maleate salts.

36. The compound of claim 22 wherein when said compound is a pharmaceutically acceptable salt said salt is selected from the group consisting of hydrochloride and maleate salts.

37. The compound of claim 34 wherein said compound is a hydrochloride salt.

38. A pharmaceutical composition, for treating cardiovascular disorders in mammals by blocking β-adrenergic receptor sites, consisting essentially of a pharmaceutically acceptable carrier and an amount effective to block β-adrenergic receptor sites on an agent selected from the group of the compounds of claim 1 and mixtures thereof.

39. A pharmaceutical composition for treating cardiovascular disorders in mammals by blocking β-adrenergic receptor sites, consisting essentially of a pharmaceutically acceptable carrier and an amount effective to block β-adrenergic receptor sites of an agent selected from the group of the compounds of claim 2 and mixtures thereof.

40. A pharmaceutical composition, for treating cardiovascular disorders in mammals by blocking β-adrenergic receptor sites, consisting essentially of a pharmaceutically acceptable carrier and an amount effective to block β-adrenergic receptor sites of an agent selected from the group of the compounds of claim 22 and mixtures thereof.

41. A pharmaceutical composition for treating hypertension disorders in mammals consisting essentially of a pharmaceutically acceptable carrier and an amount effective to treat hypertension of an agent selected from the group of the compounds of claim 1 and mixtures thereof.

42. A pharmaceutical composition for treating hypertension disorders in mammals consisting essentially of a pharmaceutically acceptable carrier and an amount effective to treat hypertension of an agent selected from the group of the compounds of claim 2 and mixtures thereof.

43. A pharmaceutical composition for treating hypertension disorders in mammals consisting essentially of a pharmaceutically acceptable carrier and an amount effective to treat hypertension of an agent selected from the group of the compounds of claim 22 and mixtures thereof.

* * * * *